US006843102B1

(12) United States Patent
Shulga et al.

(10) Patent No.: US 6,843,102 B1
(45) Date of Patent: Jan. 18, 2005

(54) GAS SENSOR ARRANGEMENT

(75) Inventors: Aleksandr Shulga, Münster (DE); Udo Schmale, Rheine (DE); Holger Müller, Münster (DE)

(73) Assignee: Gasbeetle GmbH, Recklinghausen (DE)

( * ) Notice: Subject to any disclaimer, the term of this patent is extended or adjusted under 35 U.S.C. 154(b) by 0 days.

(21) Appl. No.: 09/979,858

(22) PCT Filed: May 26, 2000

(86) PCT No.: PCT/EP00/04838

§ 371 (c)(1), (2), (4) Date: Feb. 22, 2002

(87) PCT Pub. No.: WO00/73768

PCT Pub. Date: Dec. 7, 2000

(30) Foreign Application Priority Data

May 26, 1999 (DE) .......................... 199 25 196

(51) Int. Cl.[7] .............................................. G01N 25/00
(52) U.S. Cl. .................... 73/25.01; 73/24.02; 73/24.03; 250/565
(58) Field of Search ........................... 73/25.01, 24.02, 73/24.03; 250/565

(56) References Cited

U.S. PATENT DOCUMENTS

| 3,745,349 | A | * | 7/1973 | Liston ......................... 250/565 |
| 5,341,214 | A | | 8/1994 | Wong ......................... 356/437 |
| 6,097,034 | A | * | 8/2000 | Weckstrom et al. ..... 250/495.1 |

FOREIGN PATENT DOCUMENTS

| CH | 674 264 A5 | 5/1990 | .......... G01N/21/61 |
| DE | 35 44 015 A1 | 6/1987 | .......... G01N/21/61 |
| DE | 43 07 190 A1 | 11/1994 | .......... G01N/21/61 |
| DE | 43 20 861 A1 | 1/1995 | .......... G01N/21/61 |
| DE | G 94 20 231.1 | 3/1995 | .......... G01N/21/61 |
| DE | 296 02 282 U1 | 8/1996 | .......... G01N/21/61 |
| DE | 195 20 488 C1 | 9/1996 | .......... G01N/21/35 |
| DE | 195 25 703 A1 | 1/1997 | .......... G01N/29/02 |
| DE | 296 15 100 U1 | 2/1998 | .......... G01N/21/61 |

OTHER PUBLICATIONS

International Preliminary Examination Report; PCT/EP00/04838, 2001.

\* cited by examiner

*Primary Examiner*—Hezron Williams
*Assistant Examiner*—André K. Jackson
(74) *Attorney, Agent, or Firm*—Baker Botts L.L.P.

(57) ABSTRACT

A gas sensor configuration comprises a radiation-emitting radiation device, a gas measuring chamber, a detector unit and an evaluation device. A measuring gas that contains at least one gas component is present in the gas measuring chamber. The evaluation device detects the gas component and/or its concentration depending on the output signal of the detector unit. The radiation emitting device comprises at least one source that emits a measuring radiation and at least one reference radiation source, the latter being switched on periodically to measure the aging state of the source that emits the measuring radiation. The evaluation device detects the aging of the source that emits the measuring radiation on the basis of deviations with respect to the output signals of the detector unit when the reference radiation source and the source that emits the measuring radiation are switched on, and, if necessary, compensates for the aging.

22 Claims, 13 Drawing Sheets

GAS SENSOR ARRANGEMENT

FIELD OF THE INVENTION

The invention relates to a gas sensor arrangement having a radiation device emitting radiation, a gas measuring chamber, a detector device and an evaluation device, wherein a measuring gas containing at least one gas component is situated in the gas measuring chamber and the evaluation device determines the gas component and/or its concentration depending on the output signal of the detector device.

BACKGROUND OF THE RELATED TECHNOLOGY

It is known that many gases absorb radiation particularly in the infrared wavelength range, wherein this absorption occurs at a wavelength which is characteristic for the gas in question, for example for $CO_2$ at 4.24 $\mu$m. With the aid of infrared gas sensors it is thus possible to establish the presence of a gas component or the concentration of a gas component.

Known infrared gas sensors have, for example a broadband radiation source, an absorption path or a measuring chamber, a wavelength-selective element, for example an interference filter, a Fabry-Perot filter or a grating and a radiation detector, for example a pyroelectric, a PbSe or thermophilic detector. The radiation intensity measured by the radiation detector is a measure of the concentration of the gas absorbing at the set wavelength. Instead of the broadband radiation source and the wavelength-selecting elements, the use of a selective radiation source, such as for example an LED or a laser in combination with non-wavelength-selective radiation receivers, is also known.

Photoacoustic gas sensors are also known. The operating principle of a photoacoustic gas sensor is based on the detection of the pressure change, which is produced by heating the gas molecules in the measuring chamber, by means of an acoustic detector, such as for example a microphone.

Heating is caused by the absorption of the radiation energy of the radiation source by the measuring gas molecules to be detected. One design of a photoacoustic gas sensor corresponding to the state of the art can be seen, for example from German patent 19 525 703.

The long-term stability of such infrared and photoacoustic gas sensors depends essentially on the aging of the radiation sources and on the soiling of the overall optical system. Soiling is currently prevented by suitable gas-permeable filters for keeping out contaminating particles.

To monitor the aging of the radiation source, the gas sensor or the gas sensors is periodically controlled with respect to zero point and sensitivity drift. Hence, the gas sensors are rinsed with a gas or gas mixture without the gas component to be measured in order to determine the position of the zero point. After zero-point control, they are rinsed using a gas mixture of known concentration of the gas component to be measured, wherein the measured value obtained is compared with a preset value. This calibration usually has to be carried out by trained personnel and is thus very cost-intensive.

A further possibility for monitoring aging of the radiation source of an infrared gas sensor consists in using a second radiation detector with an optical filter for the detection of the radiation intensity at the wavelength, at which a gas component of the measuring gas does not have considerable absorption (see U.S. Pat. No. 5,341,214). By forming a quotient of the two signals obtained, that is measuring signal to reference signal, aging of the radiation source is compensated. Since the detectors represent a main cost factor of the gas sensors and since double signal processing is required, such gas sensors are relatively expensive. In addition, different drift for the detectors may occur during temperature changes.

Furthermore, there are infrared gas sensors with two radiation sources, in which the light path of the one radiation source does not go through the measuring gas chamber, with which soiling of the optical system and aging of the other radiation source may be determined. However, according to principle this is only possible using a reference gas without the gas component to be measured.

Also, an arrangement is known where two light sources are arranged within the gas chamber at a different distance from the radiation detector. The two radiation sources are modulated at different frequencies and the detector signal is demodulated. The output signals of the different frequencies are divided by one another, so that the distance between both sources produces the effective light path. However, due to the fact that the radiation sources do not age uniformly (see FIG. 10), there may be an intensification of the drift of the sensor due to aging of the radiation sources.

SUMMARY OF THE INVENTION

The object of the invention is to further develop a gas sensor arrangement according to the preamble of the independent claims such that aging of the radiation source may be reliably monitored without considerable additional expense in terms of components and without the necessity of calibrating gases.

This object is achieved according to the invention by the characterising features of the independent claims in conjunction with the features of their preamble.

The aging of the measuring radiation source may be recorded by an additional radiation source, the reference radiation source, which is switched on at temporal intervals, by comparing the output signals of the detector when operating the reference radiation source to the output signal of the detector when operating the measuring radiation source. The reference radiation source thus does not serve for normal measurement, it is operated at considerable monitoring intervals for determining aging of the measuring radiation source. Aging of the reference radiation source can be ignored, since it is operated considerably more rarely than the measuring radiation source, that is at considerable temporal intervals, so that it does not age noticeably in the service life of the sensor. Cost-effective and reliable recording of aging of the measuring radiation source is possible without calibrating gas due to the design of the invention.

Advantageous further developments and improvements are possible due, to the measures indicated in the dependent claims.

The effective light path between the radiation sources and the detector is preferably the same length. The sensor calibration curves for the reference source and the measuring source are the same under these conditions.

A further advantage of a gas sensor having more than two sources lies in the considerable breakdown safety, that is if a measuring source fails, the sensor will continue to operate using the additional source. The preferred embodiment in this case is a gas sensor having 3 radiation sources, a measuring source, a reference source, an additional measuring or additional reference source. The service life of the sensor may thus be extended many times. In addition, minimum aging of the reference radiation source may be compensated by the further radiation source(s).

The number of referencing measurements and hence the aging of the reference radiation source may be reduced to a necessary minimum by simple integration of an additional low-cost radiation detector (for example Si photodiode). Aging of the measuring radiation source is thus monitored in a spectral range (for example 850 nm) by means of the additional radiation detector, and the reference radiation source is only used in the event that the radiation intensity of the measuring source measured by the low-cost detector has changed by a certain value.

BRIEF DESCRIPTION OF THE DRAWINGS

Exemplary embodiments of the invention are shown in the drawings and are illustrated in more detail in the following description.

DETAILED DESCRIPTION OF THE PREFERRED EMBODIMENT

Figure 1:
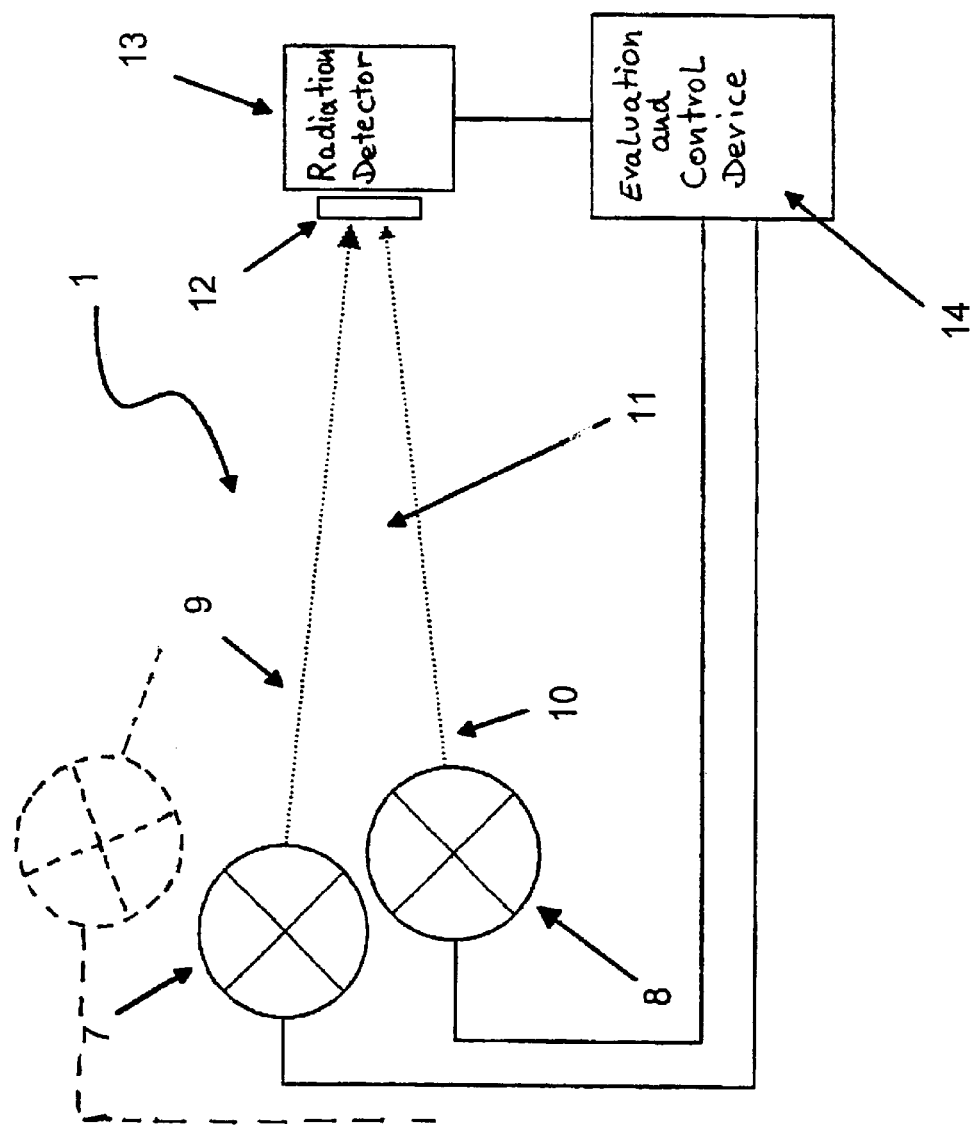
FIG. 1 shows a schematic representation of the structure of a first exemplary embodiment of a gas sensor arrangement according to the present invention having any path length between reference or measuring radiation source and detector.

The gas sensor arrangement according to FIG. 1 is designed as an infrared gas sensor arrangement and has an infrared gas sensor 1 structured conventionally as one unit, which infrared gas sensor 1 is connected to an evaluation and control device 14, for example by means of a plug arrangement.

In the schematic structure of the infrared gas sensor 1 according to FIG. 1, a measuring radiation source is designated by the reference number 7 and a reference radiation source is designated by the reference number 8. The radiation sources 7, 8 preferably have identical parameters and radiate with a broadband radiation spectrum. In gas sensor operation, the measuring radiation source 7 is used for measuring the measuring gas concentration, it may be operated continuously or in pulsed-mode operation for this. On the other hand, the reference radiation source 8 is only switched on at considerable temporal intervals to determine aging of the measuring radiation source 7. The radiation sources 7, 8 emit infrared radiation through a measuring chamber 11, where the gas to be detected or the gas mixture composed of several gas components is situated. The gas sensor may be designed as a flowed-through sensor arrangement, that is as a through-flow measuring cell, or as a sensor based on diffusion. In the first case, the gas flows through the measuring chamber 1, whereas in the second case, the gas diffuses over a membrane into the otherwise closed measuring chamber 11.

A radiation detector 13 is arranged at a distance from the radiation sources 7, 8 such that after passing through the measuring chamber 1, the radiation falls on the detector 13. An interference filter 12 lies between the gas measuring chamber 11 and the detector 13 and preferably allows through only the radiation which corresponds to the absorption wavelength of the gas to be measured. The interference filter 12 may also be integrated directly into the radiation detector housing. The absorption wavelengths for different gases are, for example 4.24 $\mu$m for $CO_2$, 3.46 $\mu$m for $CH_4$, 4.64 $\mu$m for CO, 5.3 $\mu$m for NO, 10.9 $\mu$m for freon. Of course, other optical bandpass filters or wavelength-selecting elements may be used instead of the interference filters.

The radiation detector 13 and the radiation sources 7 and 8 are connected to the evaluation and control device 14, which processes the output signals from the radiation detector 13, actuates the radiation sources 7, 8, records, takes into account the data on aging of the measuring radiation source 7 and delivers the information on the concentration of the measuring gas. The radiation sources 7, 8 each have a different path length for their optical paths 9, 10 from the radiation detector.

Figure 2:
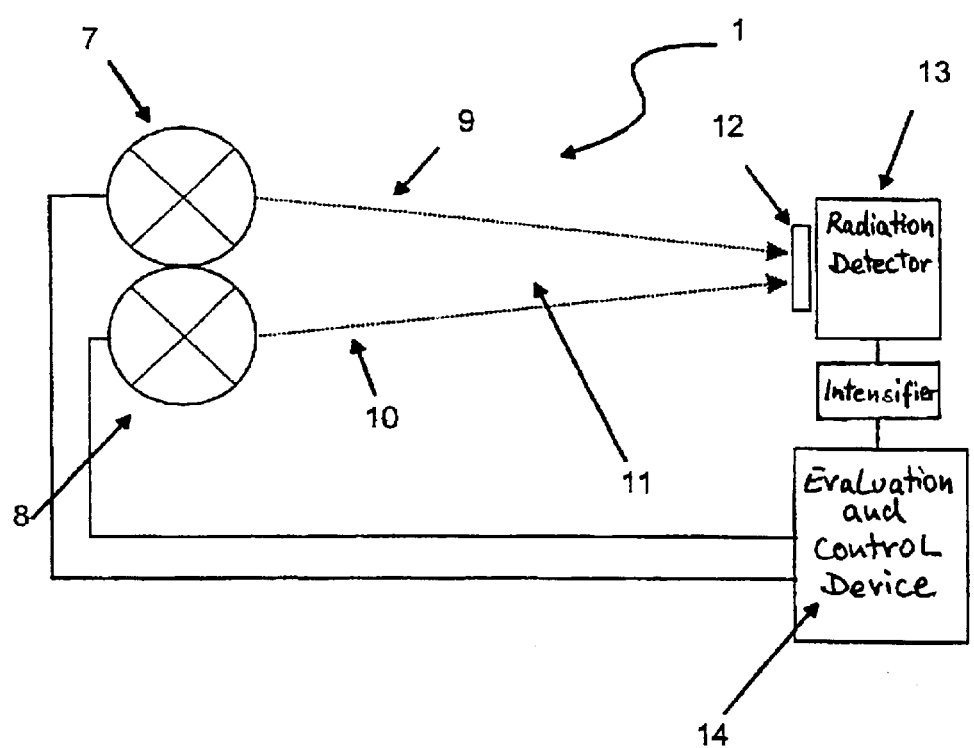
FIG. 2 shows a schematic representation of the structure of a further exemplary embodiment of a gas sensor arrangement according to the present invention having symmetrical structure.

FIG. 2 shows a further exemplary embodiment, here the radiation sources 7, 8 are preferably arranged closely next to one another and symmetrically with respect to the radiation detector 13, such that their radiation falls with approximately the same intensity on the radiation detector 13 and that the effective length of their optical paths 9 and 10 through the measuring chamber 13 is the same. Hence, both radiation sources may also be integrated in the same housing (for example two or more spiral-wound filaments in a glass bulb).

On the one hand, the infrared gas sensor 1 may be structured so that the radiation detector 13 together with the interference filter 12 is placed directly opposite the radiation sources 7, 8 and is directly irradiated by the radiation sources 7, 8. On the other hand, the light emitted by the radiation sources 7, 8 may be guided along the optical paths 9, 10 both within and outside the measuring chamber 11 by one or more reflecting surfaces and conveyed to the radiation detector 13.

The light emitted by the measuring radiation source 7 or reference radiation source 8 goes through the measuring chamber 11, the optical filter 12 and in the end falls on the radiation detector 13. Some of the light radiated through the measuring chamber in the wavelength range, which corresponds to the absorption range of the measuring gas, is absorbed by measuring gas molecules in the presence of the gas to be detected in the measuring chamber 11. The reduction thus caused in the light intensity registered by the radiation detector 13 follows the Beer-Lambert law $$I_C = I_0 \cdot \exp(-aCL)$$

a is the absorption coefficient of the gas to be measured in the transmission range of the optical filter 12,
C is the concentration of the gas to be measured in the measuring chamber 11,
L is the effective length of the radiation paths 9 or 10,
$I_0$ is the intensity of the radiation falling on the radiation detector 13 without reduction by the measuring gas molecules
$I_C$ is the intensity of the radiation falling on the radiation detector 13 in the presence of the gas to be detected in the measuring chamber 11.

The sensor is calibrated before the actual measurements, wherein the parameters, for example type and concentration of the gas, temperature and the like are known, that is at least one sensor characteristic is generated which connects the output signal of the radiation detector 13 with the measuring gas concentration in the measuring chamber 11.

The output signals of the radiation detector 13 produced during the measurement are delivered to the evaluation and control device 14, which calculates the concentration of the measuring gas using the sensor characteristic determined during the sensor calibration. The gas sensor temperature may also be recorded during the measurement and taken into account when calculating the measuring gas concentration.

The following condition applies independently of the measuring gas concentration in the measuring chamber 11 due to the arrangements of the radiation sources 7, 8 with regard to the radiation detector 13:

$$U_R = F \cdot U_M$$

Hence,
$U_M$ is the output signal of the radiation detector 13 when operating the measuring radiation source 7,
$U_R$ is the output signal of the radiation detector 13 when operating the reference radiation source 8,
F is a ratio factor, wherein preferably the radiation sources 7 and 8 are selected to be as equal as possible, which may lead to a value F=1 in a new sensor.

Since in the course of measurements, the operating time of the measuring radiation source 7 is much longer than that of the reference radiation source 8, the value of the ratio factor F changes due to the different aging of the two sources with time.

Correction of aging for any arrangement of the radiation sources 7, 8 (see FIG. 1) is set out mathematically below.

For the initial calibration during manufacture at the point in time t=0, the calibrating functions are stored for the two sources 7, 8.

(1) $U_M(0,C) = U_M(0,0)\exp(-aCL_M)$
(2) $U_R(0,C) = U_R(0,0)\exp(-aCL_R)$
where
C—is the concentration of the gas to be measured in the measuring chamber
C*—is the concentration of the gas to be measured in the measuring chamber during the correction process
$L_M$—is the effective light path of radiation from the measuring radiation source to the detector
$L_R$—is the effective light path of radiation from the reference radiation source to the detector
$U_{source}$(time, concentration):
$U_M(0,0)$, $U_R(0,0)$—is the output signal of the detector during operation of the measuring or reference source in the absence of the gas to be detected in the measuring chamber at the point in time t=0
$U_M(0,C)$, $U_R(0,C)$—is the output signal of the detector during operation of the measuring or reference source in the presence of the gas to be detected in the measuring chamber at the point in time t=0

The ratio factor F of the signals for the two sources is dependent an concentration:

$$F(0, C) = \frac{U_R(0, C)}{U_M(0, C)} = \frac{U_R(0, 0)}{U_M(0, 0)} \exp(-aC\Delta L), \Delta L = L_R - L_M \quad (3)$$

After the time t in operation, the calibrating function of the measuring source will change:

(4) $U_M(t,C) = U_M(t,0)\exp(-aCLM)$

The correction process is then carried out. At that point in time, the concentration of the gas to be measured is equal to C*. Then follows (5) $U_M(t,C^*) U_M(0,0)\exp(-aC^*L_M)$
(6) $U_R(t,C^*) = U_R(t,0)\exp(-aC^*L_R)$ Since $U_R(t,0) = U_R(0,0)$ (the reference source 8 hardly ages), equation (6) is equivalent to equation (2) and the stored calibrating function of the reference source 8 may be used for the calculation of the concentration of the gas to be determined at the point in time of the measurement t,C*.

$$C^* = \frac{-1}{aL_R} \ln\left(\frac{U_R(t, C^*)}{U_R(0, 0)}\right) \quad (7)$$

The signal value of the non-aged measuring source is calculated with the aid of this C* and equation (1). The ratio from the calculated signal of the non-aged measuring source (for which the calibrating function was determined and the actual signal of the measuring source is then calculated as the correction factor K.

$$K(t) = \frac{U_M(0, C^*)}{U_M(t, C^*)} \quad (8)$$

(9) $U_M(t,C) = 1/K \; U_M(0,C)$ for the corrected calibrating function of the measuring source follows from (4), (5) and (8).

The calibrating function (9) may then be used until the next correction process. The correction is likewise possible in the case of, for example a linear or quadratic calibrating function.

Correction of aging for a symmetrical arrangement of the radiation sources 7, 8 (see FIG. 2) is as follows:

When using two radiation sources, which are arranged symmetrically to the detector, the following signal variations with the concentration apply at the point in time t=0:

(1') $U_M(0,C) = U_M(0,0)\exp(-aCL)$
(2') $U_R(0,C) = U_R(0,0)\exp(-aCL)$

At the point in time t=0, the ratio factor F(0,C) between the two radiation sources is formed.

$$F(0, C) = \frac{U_R(0, C)}{U_M(t, C)} = \frac{U_R(0, 0)\exp(-aCL)}{U_M(0, 0)\exp(-aCL)} = \frac{U_R(0, 0)}{U_M(0, 0)} = F(0) \quad (3')$$

The ratio of the signals for the two sources is independent of concentration, since the two light paths L are of equal length,
It follows therefrom:
(4') $U_M(0,0) = 1/F(0)\, U_R(0,0)$
With the previously incorporated calibrating function (equation 1'), the following applies
(5') $U_M(0,C) = 1/F(0) U_R(0,0)\exp(-aCL)$
After the time t in operation, the calibrating function of the measuring source will change. At the point in time t at any concentration of the gas to be measured, the following applies:
(6') $U_M(t,C^*)\, U_M(t,0)\exp(-aC^*L)$
(7') $U_R(t,C^*)\, U_R(t,0)\exp(-aC^*L)$
The concentration-independent ratio factor F(t) results therefrom.

$$F(t, C^*) = \frac{U_R(t, C^*)}{U_M(t, C^*)} = \frac{U_R(t, 0)}{U_M(t, 0)} = F(t) \quad (8')$$

Since $U_R(t,0) = U_R(0,0)$ (the reference source hardly ages), the following applies
(9') $U_M(t,0) = 1/F(t)\, U_R(0,0)$
The temporal change of radiation intensity of the measuring radiation source is compensated by the formation of the ratio factor F(t). Together with equation (6') and equation (9') the following then applies for the calibrating function:
(10') $U_M(t,C) = 1/F(t)\, U_R(0,0)\exp(-aCL)$
The ratio factor F(t) is used until the next referencing.

For a non-symmetrical arrangement of the two radiation sources, for example before starting, subjected to calibration using test gas. When operating the sensor, the reference radiation source is switched on at certain times.

The algorithm described above for correction of aging of the measuring source at the point in time $t_1$ proceeds schematically as follows:

1. First of all, the detector signal $U_M(t_1)$ is measured when operating the measuring source.
2. The detector signal $U_R(t_2)$ is then determined when operating the reference source.
3. Since the reference source is rarely operated and therefore remains stable, the value $U_R(t_2)$ is used, with the aid of the stored calibrating function for the reference source, to calculate the instantaneous ambient concentration of the gas to be measured $C(t_2)$.
4. Starting from the value $C(t_2)$, the detector signal $U_M(0)$, which would correspond to that of the non-aged measuring source, is calculated with the aid of the inverse calibrating function for the measuring source.
5. Then the correction factor K is determined by comparing the values $U_M(t_1)$ and $U_M(0)$, for example as follows: $K(t_1) = U_M(0)/U_M(t_1)$.
6. The measurement with the measuring source is then repeated and the detector signal $U_M(t_3)$ is compared with the value $U_M(t_1)$ at the start of the correction process. If there is a deviation, which is greater than is allowed (the criterion is determined beforehand), the measurement must be repeated. The time intervals $(t_2-t_1)$ and $(t_3-t_1)$ should preferably be much smaller than the diffusion-related response time of the gas sensor. A virtually constant concentration of the gas to be determined is thus guaranteed during the correction process.
7. The correction factor $K(t_1)$ calculated as described above is now used to compensate the aging-related displacement of the calibrating function of the measuring source. In the present case, for example the values of the detector signal measured from now should be multiplied by the correction factor K: $U_M^{Corr} = U_M^{measured} \times K(t_1)$. The correct value of the concentration of the gas C to be measured is then calculated with the aid of the values $U_M^{corr}$ and the stored calibrating function for the measuring source.
8. The value of the correction factor $K(t_1)$ is used until the next correction process is carried out.
9. The concentration calculation is then carried out using the stored calibrating function. This may be executed, depending on the required accuracy, or required measuring range, for example with a linear, quadratic or exponential function.

To determine the ratio factor F for a symmetrical structure, the reference radiation source is likewise switched on at certain times when operating the sensor. To control whether the two effective light paths are of equal length, for example before starting, the sensor is exposed to a known gas concentration of the gas to be measured and the concentration variation with measuring or reference radiation source checked. If the variations are the same, for example only one concentration calibration is carried out using the reference source.

The algorithm for correcting aging of the measuring source at the point in time to proceeds schematically as follows:

1. First of all, the detector signal $U_M(t_1)$ is measured when operating the measuring source.
2. The detector Signal $U_R(t_2)$ is then determined when operating the reference source.
3. Determination of the ratio factor F takes place by comparing the values $U_M(t_1)$ and $U_R(t_2)$, for example as follows: $F(t_1) = U_R(t_2)/U_M(t_1)$.
4. The measurement with the measuring source is then repeated and the detector signal $U_M(t_3)$ is compared with the value $U_M(t_1)$ at the start of the correction process. If there is a deviation, which is greater than is allowed (the criterion is determined beforehand), the measurement must be repeated. The time intervals $(t_2-t_1)$ and $(t_3-t_1)$ should preferably be much smaller than the diffusion-related response time of the gas sensor. A virtually constant concentration of the gas to be determined is thus guaranteed during the correction process.
5. The ratio factor $F(t_1)$ calculated as described above is now used to compensate the aging-related displacement of the calibrating function of the measuring source. In our case, for example the values of the detector signal measured from now should be multiplied by the F factor: $U_M^{corr} = U_M^{measured} \times F(t_1)$. The correct value of the concentration of the gas C to be measured is then calculated with the aid of the values $U_M^{corr}$ and the stored calibrating function for the reference source.
6. The value $F(t_1)$ is used until the next correction process is carried out.
7. The concentration calculation is then carried out with the aid of the stored calibrating function for the reference source. This may be executed depending on the required accuracy, or required measuring range, for example with a linear, quadratic or exponential function.

Correction of aging of the measuring radiation source may be carried out by the following measures.

One possibility is the standardisation of the detector output signal when operating the measuring radiation source 7 to the value when operating the reference radiation source 8. The characteristic of the gas sensor thus relates to the detector output signal when operating the reference radiation source 8. During normal operation of the sensor, the output signal of the detector 13 is always multiplied by the ratio factor F, before the characteristic is applied to the measured values for concentration determination. Changes in the ratio factor F with time are thus automatically taken into account.

In another exemplary embodiment, a variable intensifier is connected downstream of the radiation detector 13, the intensification of which is readjusted as a function of the current ratio factor F or correction factor K from the evaluation and control device 14, so that the output signals of the intensifier are the same during operation with the measuring radiation source 7 and during operation with the reference radiation source 8. In this exemplary embodiment, the early recognition of the end of the service life of the measuring radiation source 7 or of the gas sensor is facilitated in that the later intensification reaches a maximum value as the limiting value which may not be exceeded.

In a further exemplary embodiment, the measuring radiation source 7 is designed to be regulatable, that is the radiation intensity of the measuring radiation source 7 is readjusted by the evaluation and control unit 4, so that a certain value of the ratio factor F, for example F=1, or of the correction factor, is always maintained during gas sensor operation. As long as the deviation of the ratio factor F(t) or of the correction factor K(t), measured at a point in time t does not exceed a preset limiting value from its starting value F(0) or K(0), compensation of aging is carried out by the measures described above.

However, if the deviation is too great and the preset limiting value is exceeded, a signal is produced and shown for example by the evaluation and control device 14 which indicates the end of the service life of the measuring radiation source 7 and hence conventionally of the gas sensor itself.

One advantage, of the gas sensor 1 is its greater breakdown safety. If the measuring radiation source 7 breaks down totally, the infrared gas sensor 1 may be operated by the reference radiation source 8 by way of transition until the disturbance is removed, instead of the measuring radiation source 7. In another exemplary embodiment, more than two radiation sources are used, as a result of which the service life of the sensor may be increased and additional compensation of aging may be carried out in the manner described above, for example of the reference radiation source.

Figure 3:
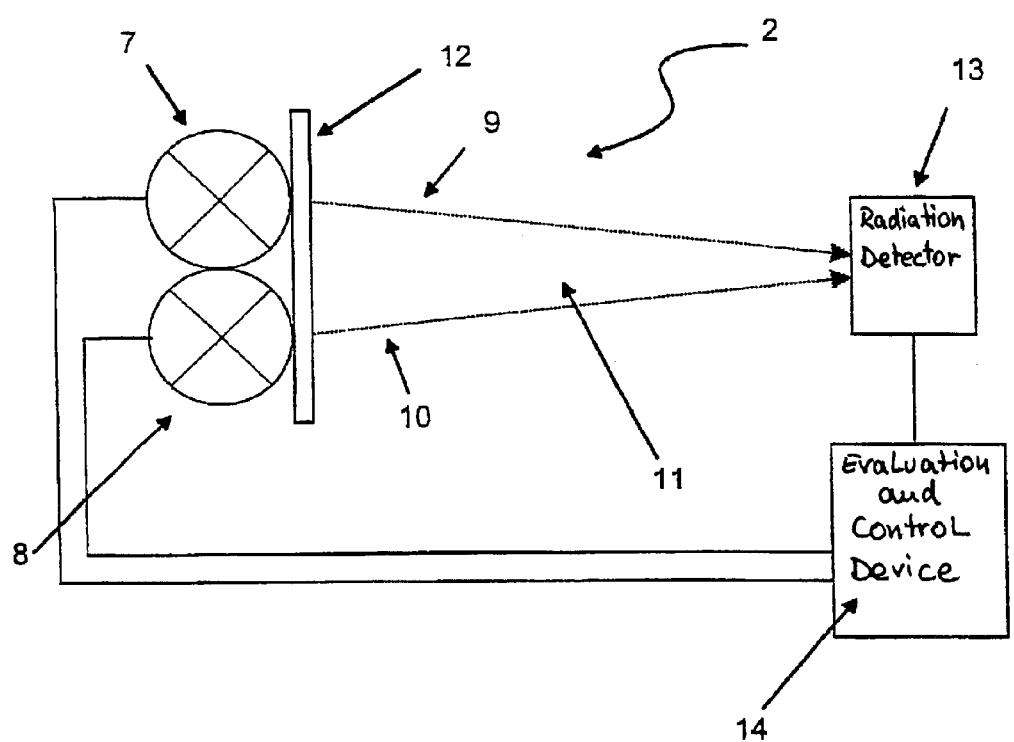
FIG. 3 shows a schematic representation of a gas sensor arrangement according to a still further exemplary embodiment of the invention, —

FIG. 3 shows an infrared gas sensor 2, wherein, differing from the infrared gas sensor 1 (FIG. 1, FIG. 2), the interference filter 12 is connected between the radiation sources 7, 8 and the gas measuring chamber 11.

Figure 4:
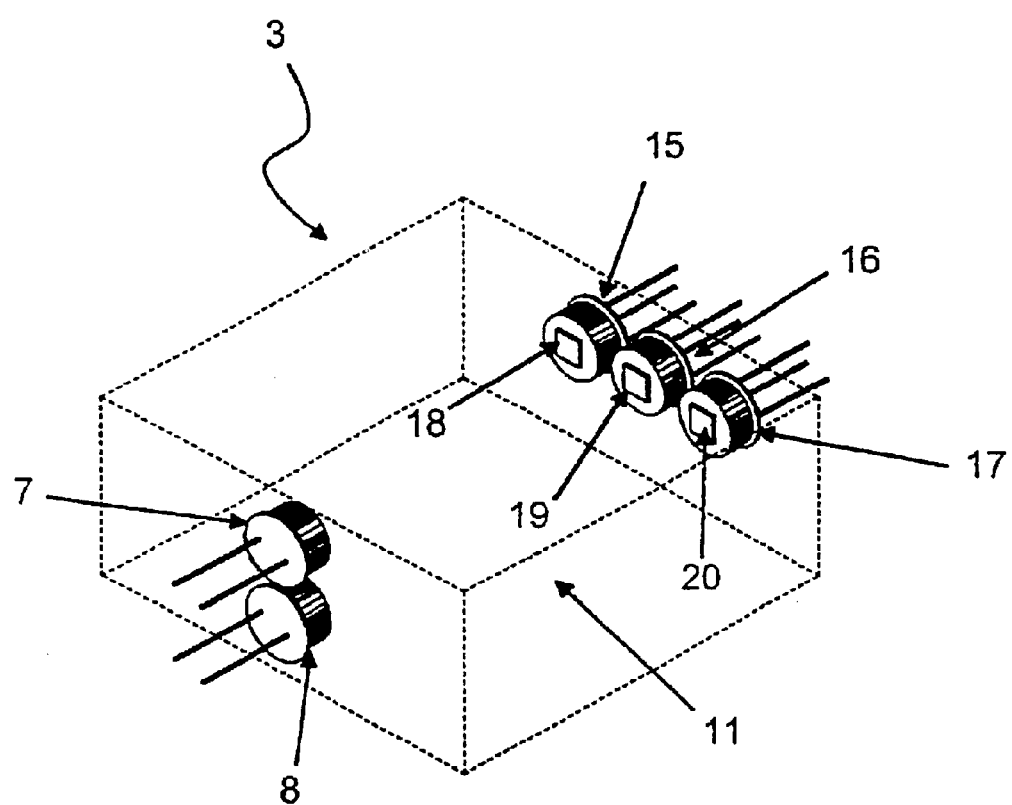
FIG. 4 shows a schematic representation of an infrared gas sensor of the invention for the detection of several gas components.

FIG. 4 shows an infrared gas sensor 3 for the simultaneous measurement of several gas components. The infrared gas sensor 3 contains several radiation detectors 15, 16, 17, which are arranged in a row opposite the radiation sources 7, 8. The measuring chamber 11 lies inbetween.

The radiation sources 7, 8 are arranged symmetrically with respect to the radiation detectors 15, 16, 17, so that the distance between the two sources and the particular radiation detector is the same and the two sources illuminate the particular radiation detector approximately equally. The radiation sources may be arranged, for example closely next to one another, so that the alignment line, on which the radiation sources is arranged, runs vertically to the alignment line, on which the radiation detectors 15, 16, 17 are placed. The infrared gas sensor 3 is designed for, for example three gases or gas components to be measured, wherein the radiation detectors 15, 16, 17 with integrated interference filters 18, 19, 20 are matched to different wavelengths corresponding to the gases to be measured. Also, only two gases or gas components may be measured and the third detector serves as reference, the latter has an interference filter for this, which is designed for a wavelength where preferably a gas does not have radiation absorption (for example e,0 m). Furthermore, it is likewise possible that all detectors are integrated into one detector housing (quad-detectors).

Figure 5:
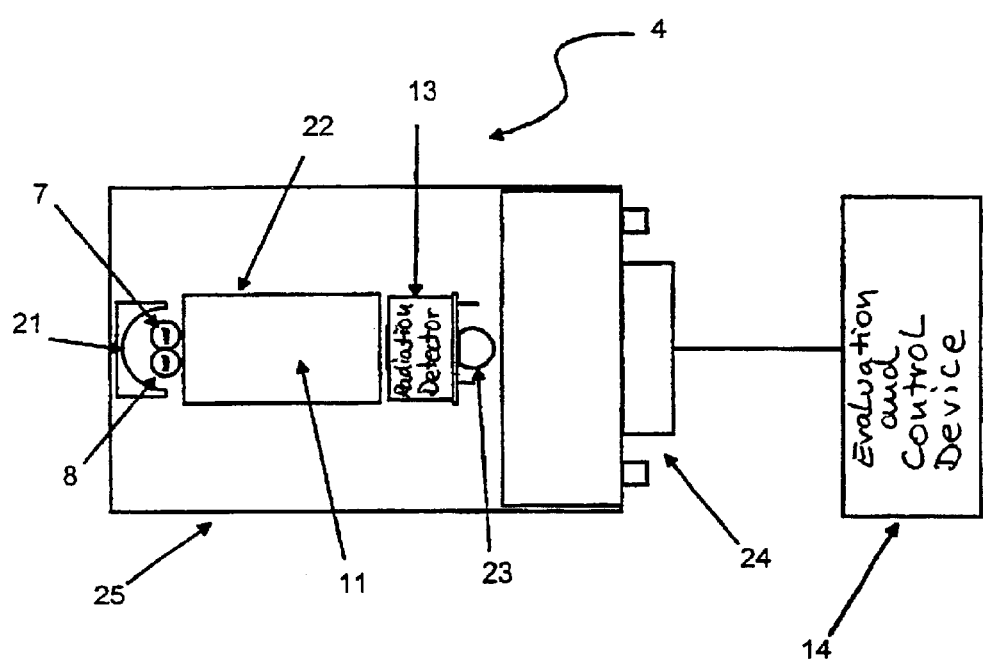
FIG. 5 shows a structural example of an infrared gas sensor arrangement according to the present invention.

FIG. 5 shows a further embodiment of an infrared gas sensor 4, which is connected to the evaluation and control device 14. The reference number 21 thus designates a reflector made from aluminum, which reflects the radiation emerging from the measuring radiation source 7 or the reference radiation source 8 into the measuring chamber 11. Hence, the radiation sources 7 and 8 are designed as miniature glow lamps of the same type. The radiation of the radiation sources 7, 8 is guided by a stainless steel tube 22 polished on the inside to the wavelength-selective radiation detector 13. The tube 22 encloses the gas measuring chamber 11.

Furthermore, a temperature sensor 23 is provided, which records the temperature of the radiation detector 13 or of the overall gas sensor 4. All components described are arranged on a plate 25 for mechanical stabilisation and for electrical contact.

The evaluation and control device 14 connected via a plug 24 processes the output signals from the radiation detector 13 and from the temperature sensor 23, actuates the radiation sources 7, 8, records the data on aging of the measuring radiation source 7 and delivers the information on the concentration of the measuring gas.

Figure 6:
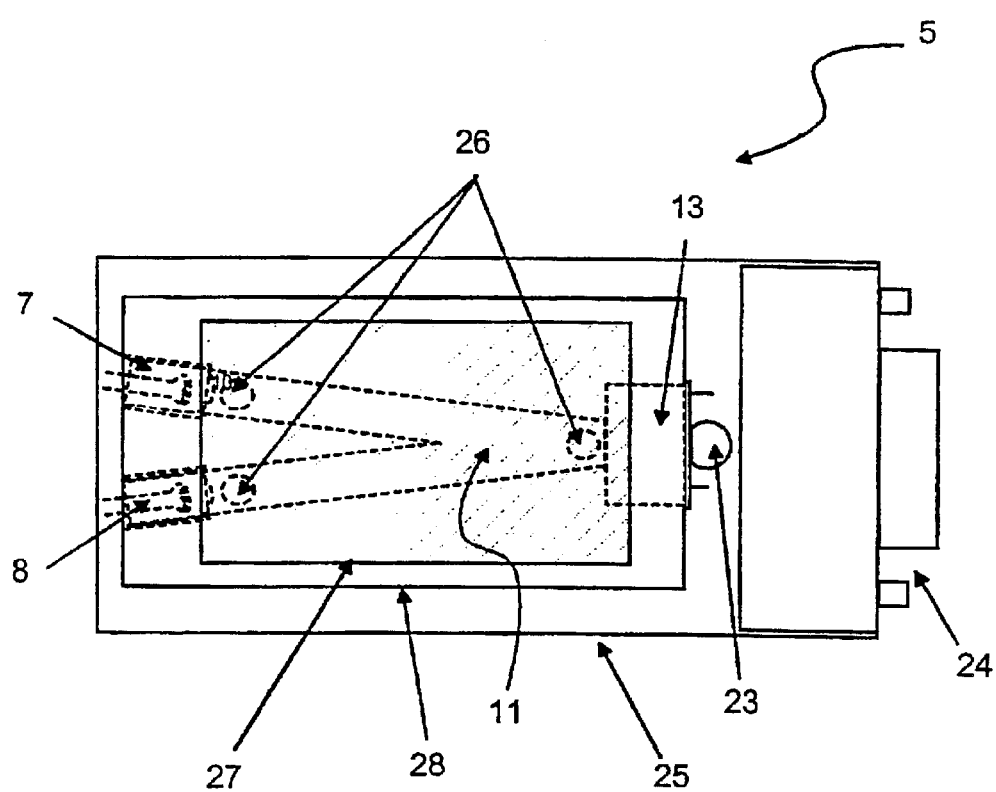
FIG. 6 shows a further exemplary embodiment of a gas sensor arrangement according to the present invention.

FIG. 6 shows schematically a further embodiment for a mechanically stable and reproducible structure of an infrared gas sensor 5. A metal block 28 is used to guarantee this reproducible structure. A bore serves to position a radiation detector 13 with an upstream optical bandpass filter or an optical bandpass filter integrated directly in the detector housing. Two optical paths, which converge on the detector 13, are bored at an angle of 8° opposite the radiation detector 13. The angle of the two optical rings may be any size, but is preferably selected so that the dimensions of the sensor remain as small as possible for a given light path. In these optical paths, which form the measuring chamber 11, two radiation sources 7 and 8 are attached so that they have the same distance from the detector. Three bores 26 vertical to the radiation paths serve as inlet for the gas to be investigated which is diffusing in. These bores are covered by means of a gas-permeable filter 27 to keep out dust and other particles. The entire metal block 29 is attached to a plate 25 for electrical contact of the radiation sources 7 and 8 and of the detector 13. A temperature sensor 23 mounted behind the detector serves to record the temperature. The electrical connection to the evaluation and control device is effected by means of the plug 24 integrated on the plate 25.

Figure 7:
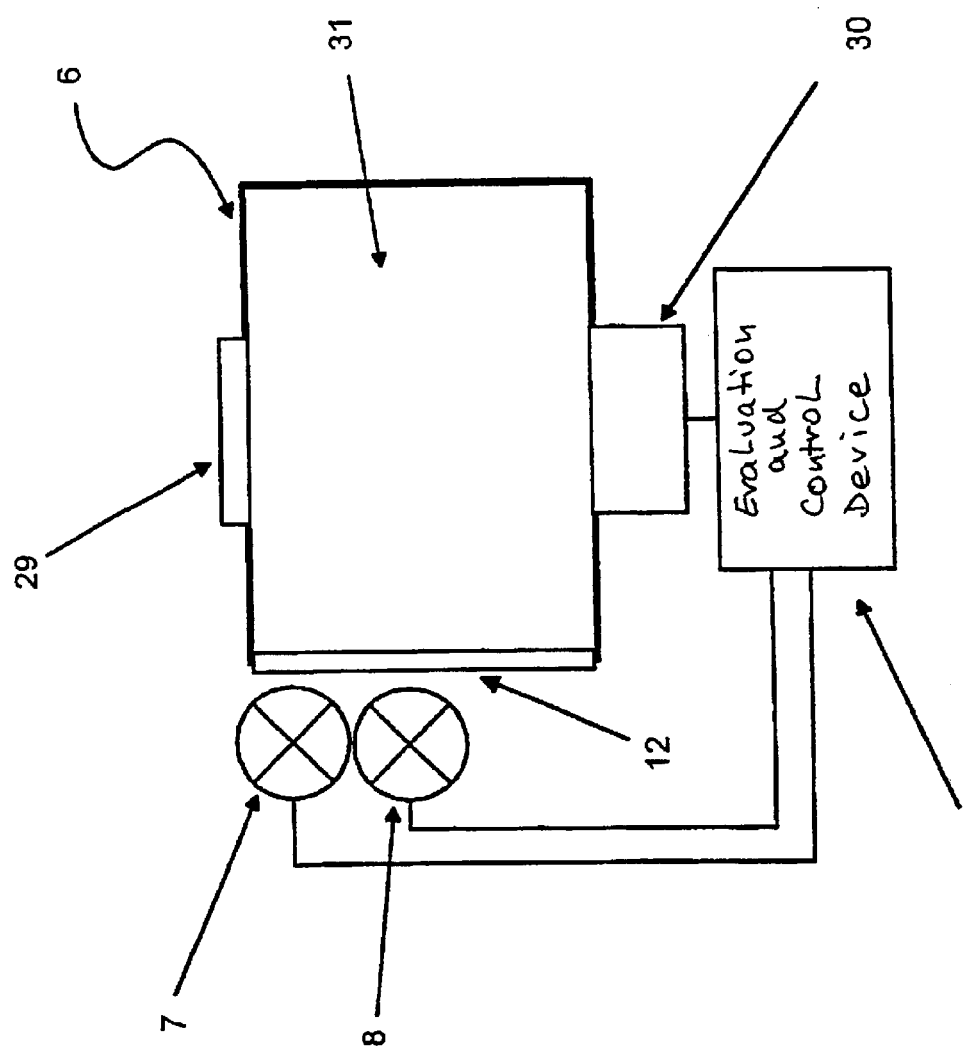
FIG. 7 shows a schematic structure of an exemplary embodiment of the invention designed as a photoacoustic gas sensor arrangement, wherein the illumination of the measuring chamber by radiation sources may be different.

FIG. 7 shows a schematic structure of a photoacoustic gas sensor 6 in cross-section with a measuring cell 31, a measuring radiation source 7 and a reference radiation source 8, an optical bandpass filter 12, an acoustic detector or microphone 30, a gas-permeable membrane 29 and an evaluation and control device 14. The radiation sources 7, 8 are preferably arranged closely next to one another, so that they irradiate the bandpass filter 12 as identically as possible. A further embodiment, in which a separate bandpass filter is assigned to each radiation source, is also possible. Illumination of the measuring cell 31 by the radiation sources is different in FIG. 7.

Figure 8:
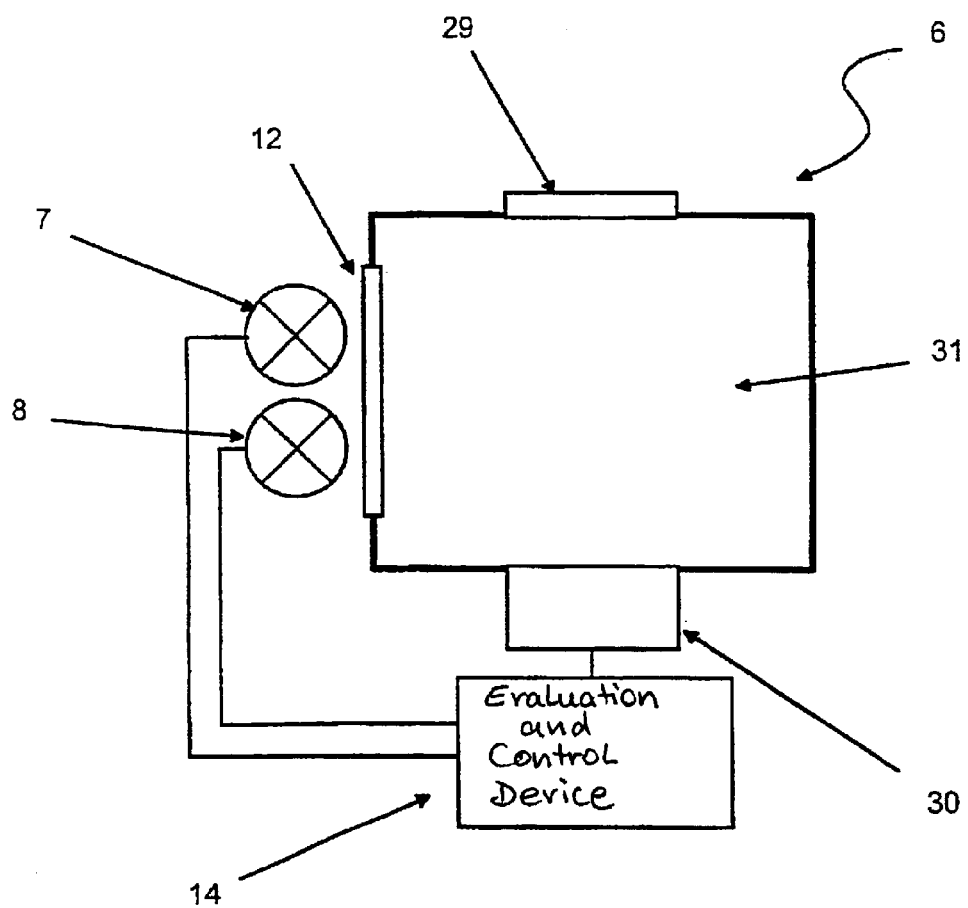
FIG. 8 shows a schematic structure of an exemplary embodiment of the invention designed as a photoacoustic gas sensor arrangement, wherein uniform illumination of the measuring chamber takes place.

In FIG. 8 the radiation sources 7, 8, in contrast to FIG. 7 with regard to the measuring cell 31, are arranged symmetrically to at least one axis of symmetry of the measuring cell 31 and/or irradiate in essentially the same solid angle.

The radiation sources 7, 8 are operated in pulsed manner, but another alternating operation is also possible. After filtering at the bandpass filter 12, the light radiated by the radiation sources 7, 8 passes into the measuring cell 31. The transmission range of the optical bandpass filter 12 is matched, so that preferably only that radiation is let through which is absorbed by the gas molecules to be measured. If the gas to be measured is situated in the vicinity of the gas sensor 6, it penetrates through the gas-permeable membrane 29 into the measuring cell 31, where it absorbs the light and is heated. As a result of the heating it expands and produces a pressure modulation, which is converted by the microphone 30 into an electrical signal. The measuring radiation source 7 is used to operate the gas sensor 6. The reference radiation source 8 is regularly used only rarely at preset time intervals in order to determine aging of the measuring radiation source 7 and to take it into account in the calculations of measuring gas concentration. Optionally, the reference radiation source 8 may be used both for monitoring the function of the microphone 30 and for sensor operation in the event of breakdown of the measuring radiation source 7.

Evaluation of the output signals from the microphone and compensation of aging are carried out as in the previous exemplary embodiments.

Figure 9:
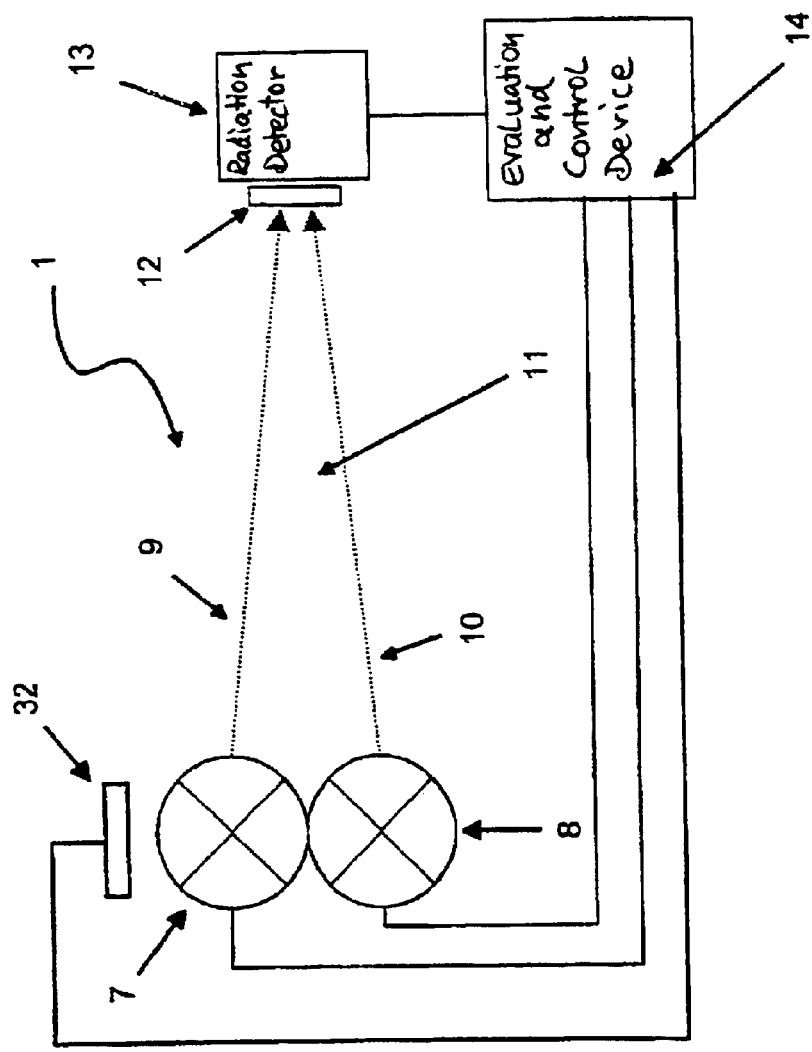
FIG. 9 shows a further exemplary embodiment of the invention with additional detector.

The number of referencing measurements and hence aging of the reference source 8 may be reduced to a necessary minimum by simple integration of an additional "low-cost", that is low-priced, radiation detector 32 (for example Si photodiode) according to FIG. 9 assigned to the measuring radiation source. Aging of the measuring radiation source 7 at a wavelength of, for example 850 nm, is thus monitored by means of the additional radiation detector 32, and the reference radiation source 8 is used only in the event that the radiation intensity of the measuring source 7, measured using the detector 32, has changed by a certain value.

Figure 10:
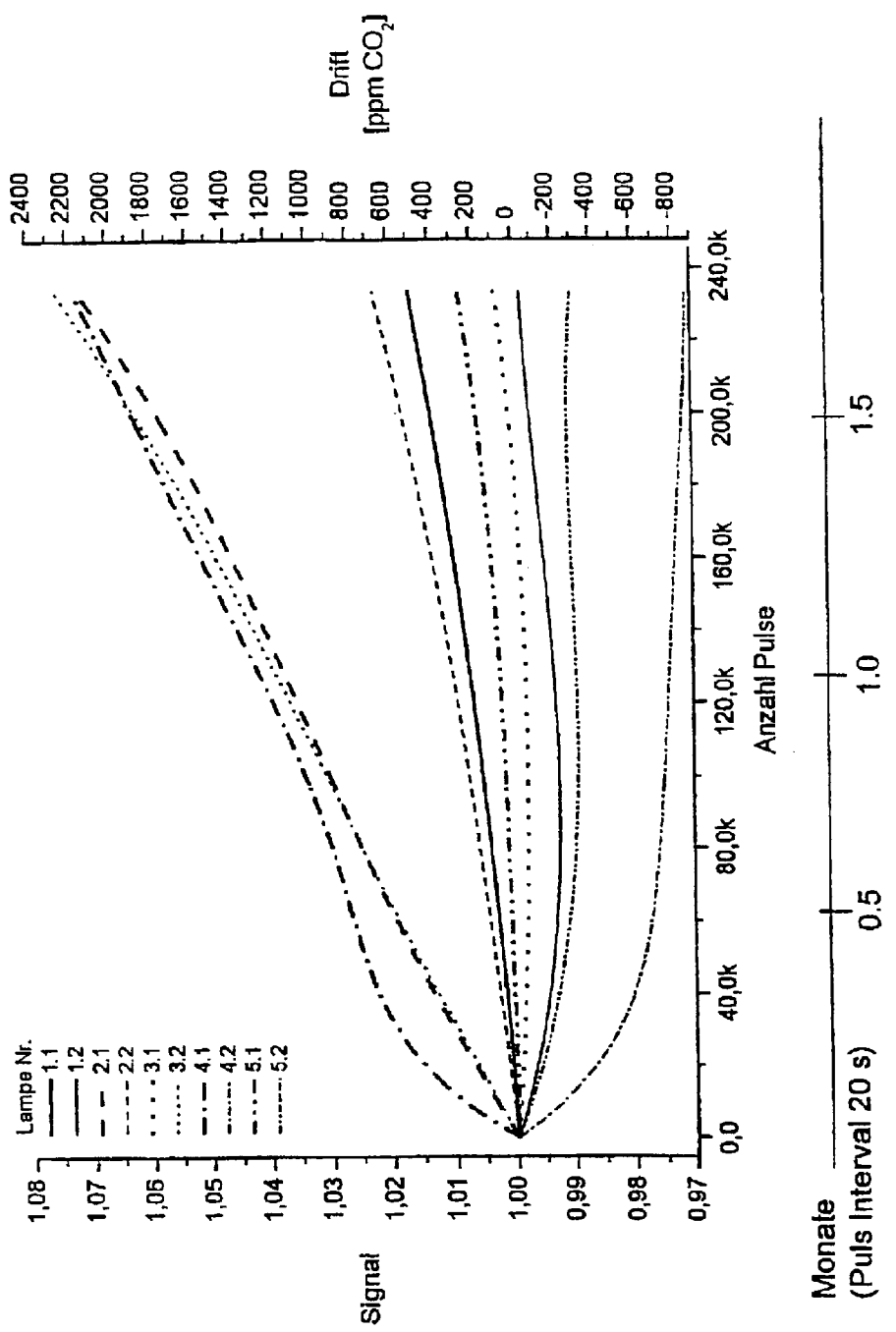
FIG. 10 shows an example of an aging curve for various lamps.

FIG. 10 shows typical aging of sub-miniature lamps using the example of the type Ti 5V 60 mA from Messrs. VCH. For the test, the lamps were switched on for about 200 ms every 20 seconds. As can be seen clearly, a general statement on aging of the source cannot be made with regard to the direction and the size of the signal change. The drift shown relates to a symmetrically structured gas sensor according to FIG. 5 having a light path length of 25 mm and a pyroelectric radiation detector of the type LHi807 TC G2 from Messrs. Perkin Elmer Optoelectronics with integrated interference filter.

Figure 11:
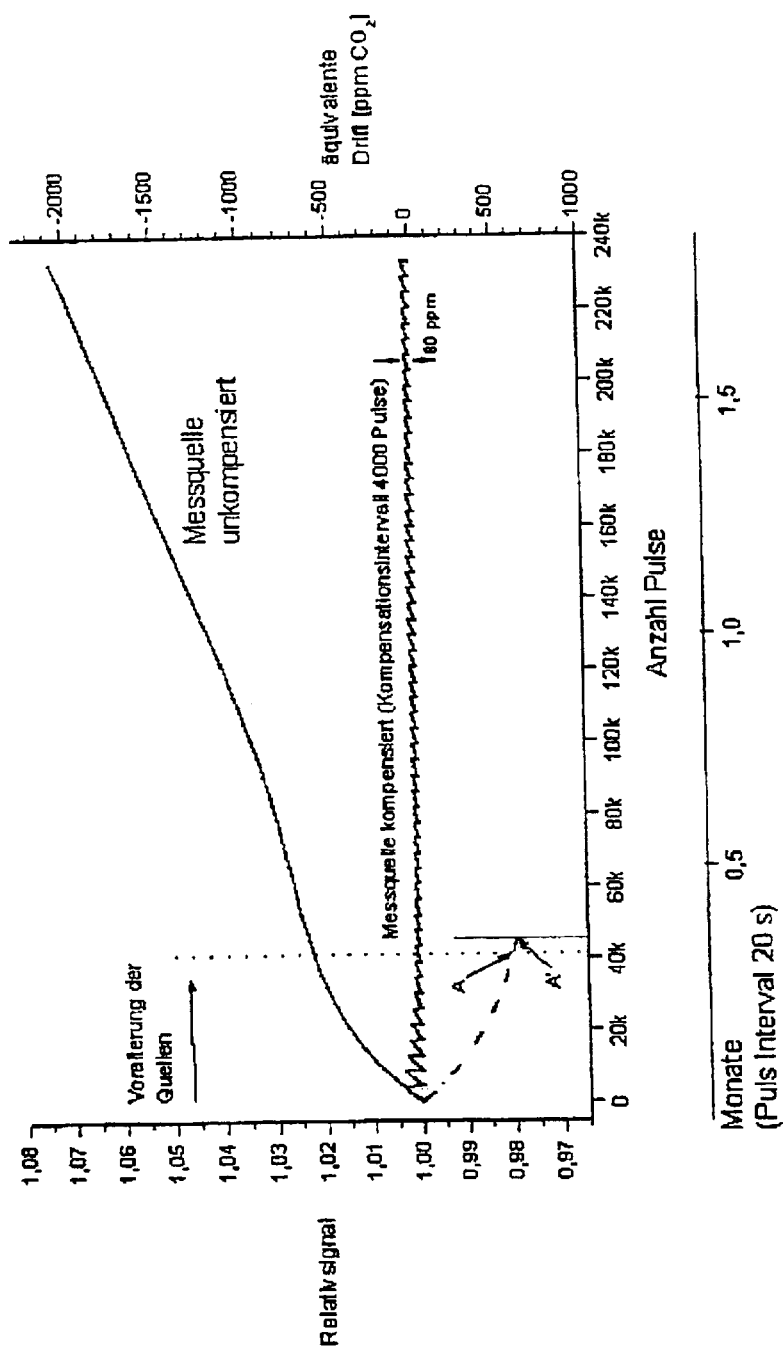
FIG. 11 shows the aging curve of a measuring source and its compensation.

FIG. 11 shows the two sources from FIG. 10 which drift most and the consequent results of drift compensation. It can be seen clearly that after prior aging by here 40,000 pulses, aging of the measuring radiation source may be compensated in an error range of about OF/=40 ppm $CO_2$.

Since the reference source at a pulse ratio of 1:4,000 (reference/measuring source) over an operating time of the sensor (for example 10 years) is in total only one day in operation (A'–A), drift of the reference source may be kept very low.

Figure 12:
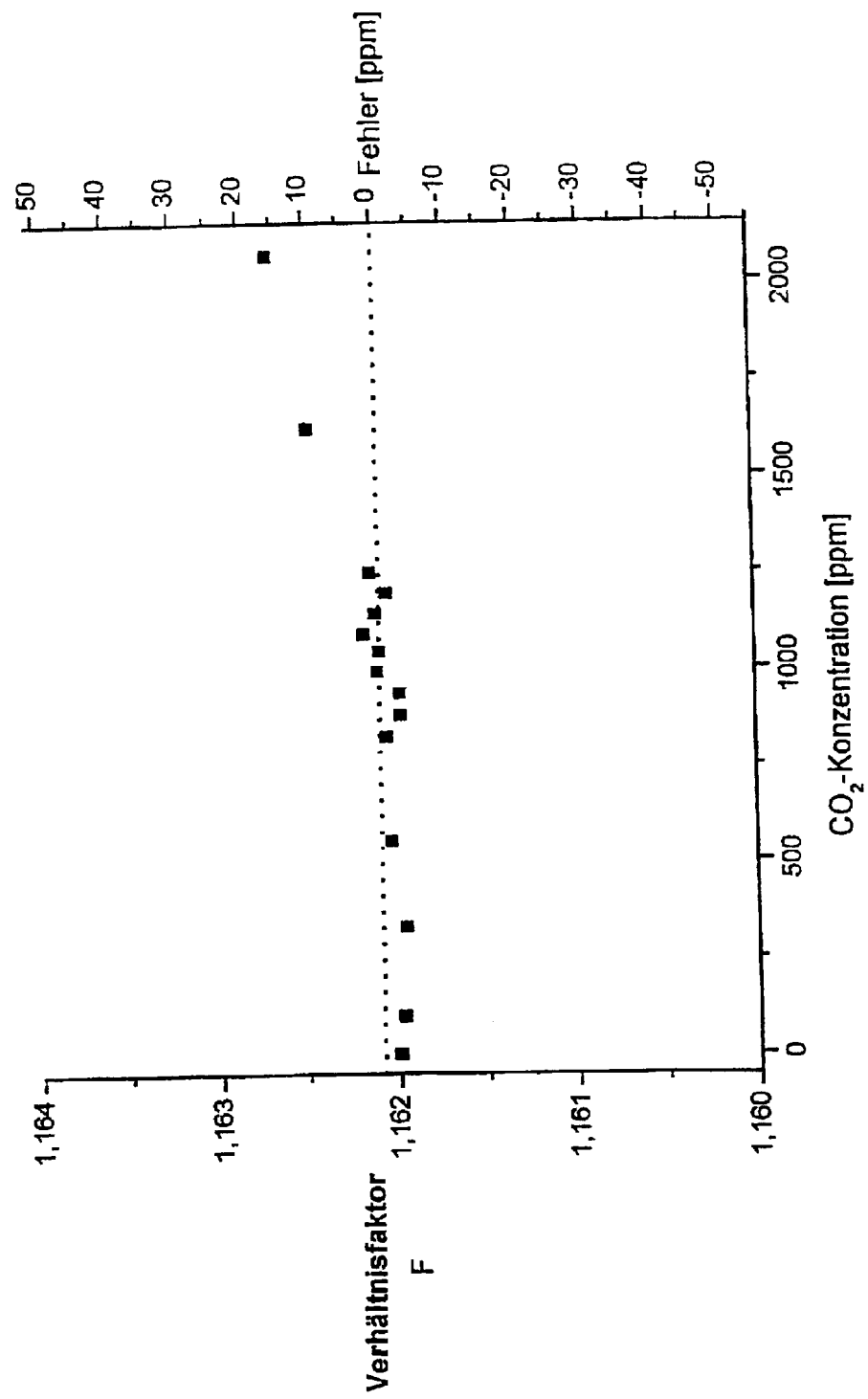
FIG. 12 shows a representation of the variation of the ratio factor with the measuring gas concentration.

FIG. 12 shows the variation of the correction factor F with the measuring gas concentration in the gas measuring chamber for a symmetrically structured gas sensor according to FIG. 5 having sources of the type VCH T1 5V 115MA and a radiation detector of the type LHi807 TC G2 from Messrs. Perkin Elmer Optoelectronics with integrated interference filter for $CO_2$. As can be seen clearly, the display error is a maximum 15 ppm $CO_2$ due to the variation of the correction factor F of this sensor.

Figure 13:
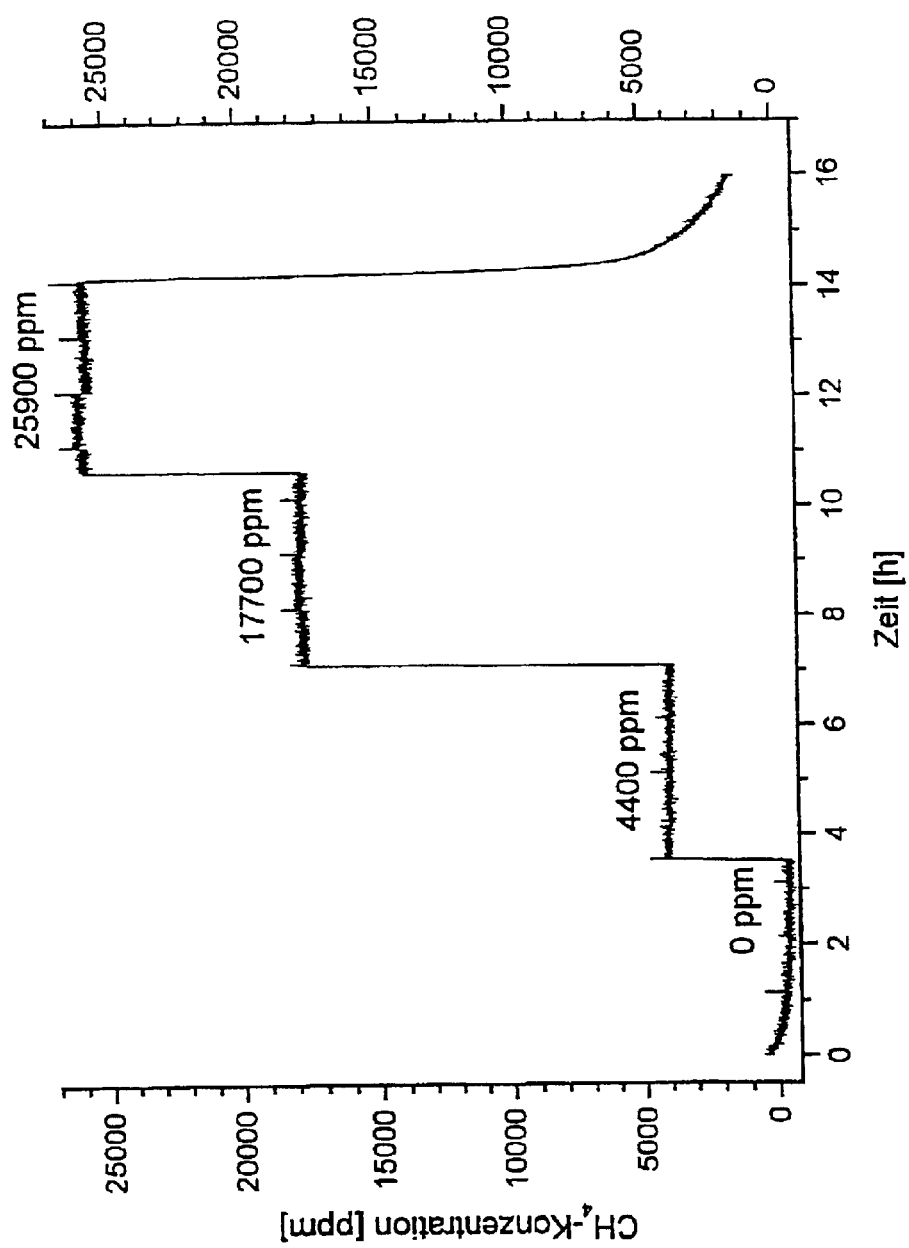
FIG. 13 shows a representation of the measured results of a sensor according to FIG. 5 over time.

FIG. 13 shows the measured results of a symmetrically structured gas sensor according to 3:3 FIG. 5 with sources of the type VCH T1 5V 115 MA and a radiation detector of the type LHi807 TC G2 from Messrs. Perkin Elmer Optoelectronics with integrated interference filter for CH4. The measuring source was thus referenced every hour.

A further cause of the long-term instability of an IR gas sensor is a possible temporal change in voltage, which is used to operate the radiation source. Deviations of the actual value of this voltage from the value preset during calibration, lead to a change in the radiation intensity of the source and accordingly to a temporal change of the sensor signal.

Since the radiation intensity of the radiation sources depends on the excitation voltage, and since the latter may drift over time depending on the type of components used, compensation for this drift may possibly be required. According to the invention, a plurality of possibilities is available to realise the required drift compensation, In order to facilitate this compensation, during sensor operation depending on the measurements record used, the voltage applied to the radiation source is measured before, during or after switching on the source and compared to the initial value of voltage determined during calibration. The source voltage changes determined in this way are then used explicitly to equalise or compensate the changes in the signal of the sensor thus caused. The following technical solutions may be used for this:

1. During sensor manufacture, calibration of the detector output signal with respect to the changes in source voltage is determined for each radiation source used in the sensor and stored (U calibration). Later during sensor operation, these data are used to compensate the drift of the source voltage occurring with time. For slight changes in source voltage from its initial value, there is for example linear variation of the detector signal with the value of the applied source voltage, although other possibilities may also exist. The required U calibration is carried out together with the temperature and concentration calibration of the sensor. The detector signal for several (preferably two) values of applied source voltage in zero air (concentration of the gas to be measured is zero) and optionally for at least one known concentration of the gas to be measured are determined for this and the function resulting therefrom is stored. For example, measurement takes place at the initial value of the source voltage and the second at a slightly different voltage value. Technically, carrying out this U calibration can be achieved in different ways, for example: a) it is possible to produce different source voltages directly with the sensor circuit adapted accordingly, which is controlled by the microcontroller belonging to the sensor; b) on the other hand, for U calibration in house, the required variable voltage values at the calibration state may be applied externally to the sensor and then stored as calibration data (U calibration).

2. If radiation sources of a certain type are used in sensor manufacture, it is possible to determine a statistically average variation of the detector output signal with the source voltage by a series test for different sources of the same charge or of the same type. The drift of the source voltage for all sensors having lamps of this type or this charge is then compensated by this function during sensor operation.

What is claimed is:

1. Gas sensor arrangement comprising: a radiation device emitting radiation, a gas measuring chamber, a detector device and an evaluation device, wherein a measuring gas containing at least one gas component is situated in the gas measuring chamber and the evaluation device determines the gas component and/or its concentration depending on the output signal of the detector device, wherein the radiation device has at least one measuring radiation source and at least one reference radiation source having the same wavelength as the measuring radiation source, and wherein the reference radiation source is inactive most of the time and is switched on at great time intervals to check the aging state of the measuring radiation source, the evaluation device establishes aging of the measuring radiation source from deviations with respect to the output signals of the detector device when the reference radiation source is switched on and the measuring radiation source is switched on.

2. Gas sensor arrangement according to claim 1, wherein the detector device includes at least one radiation detector, which records the change in intensity when the gas measuring chamber is irradiated, or a microphone, which records the pressure change of the measuring gas by absorption of the radiation entering the gas measuring chamber.

3. Gas sensor arrangement according to claim 1, wherein the measuring radiation source and the reference source are arranged such that their optical paths have the same effective light path length from the detector device, or that they lie symmetrically to an axis of symmetry of the gas measuring chamber.

4. Gas sensor arrangement according to claim 1, wherein the gas measuring chamber has at least one axis of symmetry, and in that the detector lies on one of these axes of symmetry, and in that the sources are arranged symmetrically to this axis of symmetry at the same distance from the detector.

5. Gas sensor arrangement according to claim 1, wherein the gas measuring chamber has at least one axis of symmetry and one light-inlet window, which is in particular a bandpass filter, which is arranged symmetrically to one of these axes of symmetry, and in that the sources are arranged symmetrically to this axis of symmetry at the same distance from the light-inlet window.

6. Gas sensor arrangement according to claim 1, wherein the evaluation circuit determines aging due to the change in a ratio of the particular output signals of the detector device when the measuring radiation source is switched on and when the reference radiation source is switched on.

7. Gas sensor arrangement according to claim 1, wherein at least one wavelength-selective element is provided, the wavelength range of which is matched to the measuring gas, and in that it is assigned between radiation sources and gas measuring chamber and/or at least one detector of the detector device.

8. Gas sensor arrangement according to claim 7, wherein several radiation detectors having different wavelength-selective elements are provided to measure different gas components and/or their concentration.

9. Gas sensor arrangement according to claim 7, wherein the wavelength-selective element is designed as an interference filter integrated into the detector or connected upstream of the detector.

10. Gas sensor arrangement according to claim 1, wherein the radiation strength of the measuring radiation source can be regulated to compensate aging.

11. Gas sensor arrangement according to claim 1, wherein an intensifier which can be regulated in its intensification is connected downstream of the particular detector to compensate aging of the measuring radiation source.

12. Gas sensor arrangement according to claim 1, wherein the evaluation device takes into account aging of the measuring radiation source in the determination of concentration by calculation depending on the deviations.

13. Gas sensor arrangement according to claim 1, wherein a radiation detector, which measures the change in the measuring radiation source caused by aging in a spectral range which differs from the absorption band of the gas to be measured, is assigned to the measuring radiation source, and in that the reference radiation source is then used if the change exceeds a preset value.

14. Gas sensor arrangement according to claim 1, wherein at least three radiation sources are provided.

15. Gas sensor arrangement according to claim 1, wherein a monitoring unit is provided to monitor the operating voltage of the radiation source and a control/regulating unit is provided to readjust and/or compensate the voltage on deviation.

16. Gas sensor arrangement comprising:
   a radiation device emitting radiation having at least one measuring radiation source and at least one reference radiation source having the same wavelength as the measuring radiation source,
   a gas measuring chamber,
   a detector device,
   an evaluation device for switching on the reference radiation source at great time intervals thereby keeping the reference radiation source inactive for most of the time to check the aging state of the measuring radiation source and for compensating the aging state.

17. Method of operating a gas sensor arrangement for measuring a gas comprising the steps of:
   providing a gas measuring chamber,
   providing a measuring radiation source;
   providing a reference radiation source having the same wavelength as the measuring radiation source;
   switching on the reference radiation source at temporal intervals thereby keeping the reference radiation source inactive for most of the time for determining the aging state of the measuring radiation source;
   compensating the measuring radiation source according to the determined aging state.

18. Method according to claim 17, wherein the step of compensating comprises the step of regulating the radiation strength of the measuring radiation source.

19. Method according to claim 17, further comprising the steps of recording the change in intensity when a gas is entering the gas measuring chamber.

20. Method according to claim 17, further comprising the steps of recording the pressure change of the measuring gas by absorption of the radiation entering the gas measuring chamber.

21. Gas sensor arrangement according to claim 1, wherein the evaluation device compensates the determined aging of the measuring radiation source.

22. Method according to claim 17, wherein the reference source is turned on with respect to the measuring source in ratio of 1 to 4000.

* * * * *